(12) United States Patent
Toda et al.

(10) Patent No.: US 9,084,305 B2
(45) Date of Patent: Jul. 14, 2015

(54) LIGHTING SYSTEM AND LIGHTING CONTROL DEVICE EQUIPPED FOR THE LIGHTING SYSTEM

(71) Applicant: PANASONIC CORPORATION, Osaka (JP)

(72) Inventors: Naohiro Toda, Osaka (JP); Hiroki Noguchi, Hyogo (JP); Tadashi Nishimura, Kyoto (JP); Shinsuke Nishioka, Osaka (JP); Toshikazu Kawashima, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 187 days.

(21) Appl. No.: 13/760,211

(22) Filed: Feb. 6, 2013

(65) Prior Publication Data

US 2013/0229113 A1  Sep. 5, 2013

(30) Foreign Application Priority Data

Mar. 2, 2012  (JP) ................................ 2012-046881

(51) Int. Cl.
 H05B 37/02 (2006.01)
 H05B 33/08 (2006.01)
(52) U.S. Cl.
 CPC .............. *H05B 37/02* (2013.01); *H05B 33/086* (2013.01); *H05B 37/0281* (2013.01); *H05B 33/0818* (2013.01); *Y02B 20/42* (2013.01)
(58) Field of Classification Search
 USPC ................................ 315/185 S, 291, 307–326
 See application file for complete search history.

(56) References Cited

U.S. PATENT DOCUMENTS

| 2004/0264193 | A1  | 12/2004 | Okumura |
| 2008/0084169 | A1* | 4/2008  | Wendt et al. ................... 315/297 |
| 2010/0084996 | A1* | 4/2010  | Van De Sluis et al. ........ 315/312 |
| 2010/0188418 | A1  | 7/2010  | Sakai et al. |
| 2011/0140633 | A1  | 6/2011  | Archenhold |
| 2012/0086338 | A1* | 4/2012  | Kim ................................ 315/86 |
| 2013/0043801 | A1* | 2/2013  | Kuwu ........................... 315/210 |

FOREIGN PATENT DOCUMENTS

| CN | 101788342 | 7/2010 |
| CN | 102177395 | 9/2011 |
| JP | 2000-252084 | 9/2000 |
| JP | 2005-228753 | 8/2005 |
| JP | 2008-258169 | 10/2008 |
| JP | 2011-23339 | 2/2011 |
| JP | 2011-29092 | 2/2011 |

OTHER PUBLICATIONS

China Office action, dated Sep. 30, 2014 along with an English translation thereof.
Japan Office action, mail date is Apr. 28, 2015.

* cited by examiner

*Primary Examiner* — Tuyet Vo
(74) *Attorney, Agent, or Firm* — Greenblum & Bernstein, P.L.C.

(57) ABSTRACT

A lighting system includes a lighting load and a lighting control device. The lighting control device is configured to adjust a light output of the lighting load to a first light output corresponding to a first correlated color temperature and a first illuminance in a first time slot, and to decrease the light output of the lighting load up to a second light output corresponding to a second correlated color temperature and a second illuminance with the passage of time in a second time slot after the first time slot.

18 Claims, 7 Drawing Sheets

LIGHTING SYSTEM AND LIGHTING CONTROL DEVICE EQUIPPED FOR THE LIGHTING SYSTEM

TECHNICAL FIELD

The invention relates to a lighting system (a lighting system for correlated color temperature and dimming control) configured to adjust a light output of a lighting load to a light output corresponding to predetermined correlated color temperature and illuminance, and a lighting control device equipped for the lighting system.

BACKGROUND ART

Japanese Patent Application Publication Number 2000-252084 A (hereinafter referred to as a "Document 1") discloses a lighting system configured to produce light environment suitable for a human biological rhythm such as a circadian rhythm or the like all through the day. The lighting system includes a lighting fixture capable of emitting a high illumination light, a middle illumination light and a low illumination light, and a control device configured to perform lighting control of the lighting fixture. The control device performs a lighting control of the lighting fixture, thereby allowing the lighting fixture to emit a high illumination light in a first time slot from morning to almost early-evening. The control device then allows the lighting fixture to emit a middle illumination light in a second time slot from the early-evening to bedtime, where at least average illuminance on a temporal axis of the middle illumination light is lower than a maximum illuminance in the first time slot. The control device further allows the lighting fixture to emit a low illumination light in a third time slot from the bedtime to next morning, where an average illuminance of the low illumination light is lower than a maximum illuminance in the second time slot.

The lighting system of Document 1 is mainly directed to a facility such as a hospital room in which (a) patients stay(s) for an almost whole day from wake time to bedtime. Twenty four hours of a day are divided into three time slots (three periods), namely a time slot from morning to early-evening, a time slot from the early-evening to bedtime, and a time slot from the bedtime to next morning. Illuminances to be secured for the time slots are define as high, middle and low illuminances.

Setting of the time slots and lighting control in each time slot do not take into consideration working hours at a workplace such as an office, a workshop or the like. That is, the lighting control does not take into consideration a biological rhythm in working hours from morning to early-evening or night in particular.

In recent years, energy-saving is desired. It is therefore important to balance the light environment suitable for the biological rhythm with energy-saving in lighting control for working hours.

SUMMARY OF INVENTION

It is an object of the present invention to balance light environment suitable for a biological rhythm with energy-saving in lighting control at a workplace for working hours.

A lighting system (A) of the present invention comprises a lighting load (2) and a lighting control device (1). The lighting control device (1) is configured: to adjust a light output of the lighting load (2) to a first light output corresponding to a first correlated color temperature and a first illuminance in a first time slot; and to decrease the light output of the lighting load (2) up to a second light output with the passage of time in a second time slot after the first time slot, the second light output corresponding to a second correlated color temperature and a second illuminance. Preferably, the first time slot is in a range from a time before noon to one o'clock after noon, and the second time slot is a time slot after noon, set after or just after the first time slot.

In an embodiment, the lighting load (2) comprises a plurality of light source elements having different kinds of correlated color temperatures. The lighting control device (1) is configured to adjust a correlated color temperature and an illuminance obtained from the lighting load (2) by adjusting each light output of the light source elements.

In an embodiment, the lighting control device (1) is configured to cooperatively decrease, in the second time slot, a correlated color temperature and an illuminance obtained from the lighting load (2).

In an embodiment, the first correlated color temperature is higher than a color temperature of neutral white color.

In an embodiment, the first correlated color temperature is equal to or lower than a color temperature of daylight color.

In an embodiment, the first illuminance is a horizontal illuminance of 500 lx or more in an installation space of the lighting load (2).

In an embodiment, the start of the second time slot is a time between one and three o'clock after noon.

In an embodiment, the second correlated color temperature is lower than a color temperature of neutral white color.

In an embodiment, the second correlated color temperature is higher than a color temperature of light bulb color.

In an embodiment, the second illuminance is a horizontal illuminance of 300 lx or more and 500 lx or less in the installation space of the lighting load (2).

In an embodiment, the lighting control device (1) is further configured to decrease the light output of the lighting load (2) to a third illuminance lower than the first illuminance in a third time slot between the first and second time slots.

In an embodiment, the lighting system (A) further comprises a human detector (1c) configured to detect the presence or nonpresence of a person in an installation space of the lighting load (2). The lighting control device (1) is configured: to adjust a light output of the lighting load (2) to the first light output in the first time slot and also to decrease the light output of the lighting load (2) up to the second light output with the passage of time in the second time slot, when the human detector (1c) is detecting the presence of a person; and to change the first light output to a light output corresponding to the first correlated color temperature and a lower illuminance than the first illuminance in the first time slot and also to change the second light output to a light output corresponding to the second correlated color temperature and a lower illuminance than the second illuminance in the second time slot, when the human detector (1c) is detecting the nonpresence of a person.

In an embodiment, the lighting system (A) further comprises a luminance sensor (1d) configured to sense illuminance in an installation space, capable of receiving light from outside, of the lighting load (2). The lighting control device (1) is configured to control the light output of the lighting load (2) based on the illuminance sensed with the luminance sensor (1d).

In an embodiment, the lighting control device (1) is configured to adjust the light output of the lighting load (2) to a fourth illuminance lower than the first illuminance in a fourth time slot just before the first time slot.

A lighting control device (1) of the present inventions is equipped for the lighting system (A).

The present invention emits a light corresponding to the first correlated color temperature (e.g., a high correlated color temperature) and the first illuminance (e.g., a high illuminance) in the first time slot (e.g., from a time before noon to near to noon). The present invention then decreases the light corresponding to the first correlated color temperature (e.g., the high correlated color temperature) and the first illuminance (e.g., the high illuminance) to a light corresponding to the second correlated color temperature (e.g., a low correlated color temperature) lower than the first correlated color temperature and the second illuminance (e.g., a low illuminance) lower than the first illuminance with the passage of time (e.g., gradually) in the second time slot (e.g., afternoon). It is therefore possible to balance light environment suitable for a biological rhythm with energy-saving in lighting control at a workplace for working hours.

BRIEF DESCRIPTION OF DRAWINGS

Preferred embodiments of the invention will now be described in further details. Other features and advantages of the present invention will become better understood with regard to the following detailed description and accompanying drawings where.

DESCRIPTION OF EMBODIMENTS

First Embodiment

Figure 1:
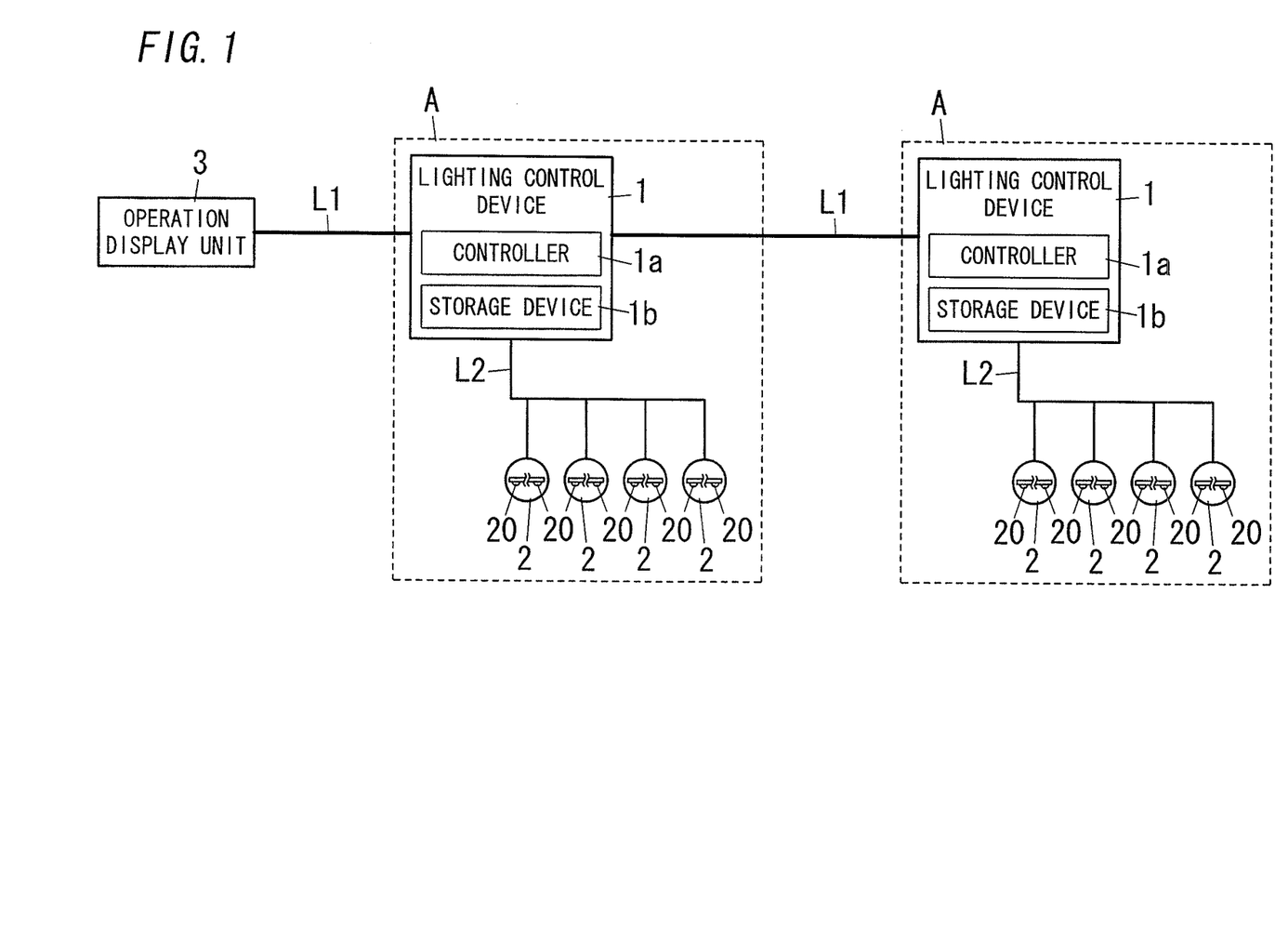
FIG. 1 is a block diagram including a lighting system equipped with a lighting control device, in accordance with a first embodiment of the present invention.

In the first embodiment, a lighting system includes a lighting control device and at least one lighting load. FIG. 1 shows an example of a system including a plurality of (e.g., two) lighting systems (A) and an operation display unit 3.

As shown in FIG. 1, each lighting system (A) includes a lighting control device 1 and a plurality of (e.g., four) lighting loads 2 each of which is capable of toning for adjusting a correlated color temperature of a light emitted therefrom and of dimming. Each lighting control device 1 of the lighting systems (A) is connected to the operation display unit 3 through a communication line (L1) and is configured to communicate with the operation display unit 3.

In a lighting systems (A), the lighting control device 1 is connected with lighting loads 2 through a communication line(s) (L2) and is configured to communicate with the lighting loads 2. Each lighting load 2 includes a plurality of light source elements (e.g., LEDs) 20 having different kinds of correlated color temperatures. For example, each lighting load 2 includes at least one first light source element and at least one second light source element. The lighting control device 1 also includes a controller 1a and a storage unit 1b. The storage unit 1b is configured to store, for example, schedule information set through the operation display unit 3. The schedule information contains relation data of predetermined time slots and light outputs respectively assigned to the time slots, and each of the light outputs is used to define each light output of light source elements 20 of each lighting load 2. The controller 1a is configured to perform toning and diming of each lighting load 2 based on the schedule information stored in the storage unit 1b.

In an example, each lighting load 2 includes, as light source elements, different kinds of (e.g., two or three different) LED devices 20 of which correlated color temperatures are different from each other. The controller 1a supplies a control signal to each of corresponding LED devices 20 in accordance with the schedule information to increase or decrease each light output (luminescence amount) of the corresponding LED devices 20, thereby performing toning and dimming of each lighting load 2. As an example, each lighting load 2 may include other light sources such as fluorescent lamps or the like in place of the LED devices.

The operation display unit 3 includes an LCD (liquid crystal display) touch screen, manual operation buttons and the like. The operation display unit 3 is configured to communicate with one or more lighting control devices 1 through the communication line (L1).

Lighting control which the lighting control device 1 performs for working hours at a workplace such as an office, a workshop or the like is explained.

Figure 2:
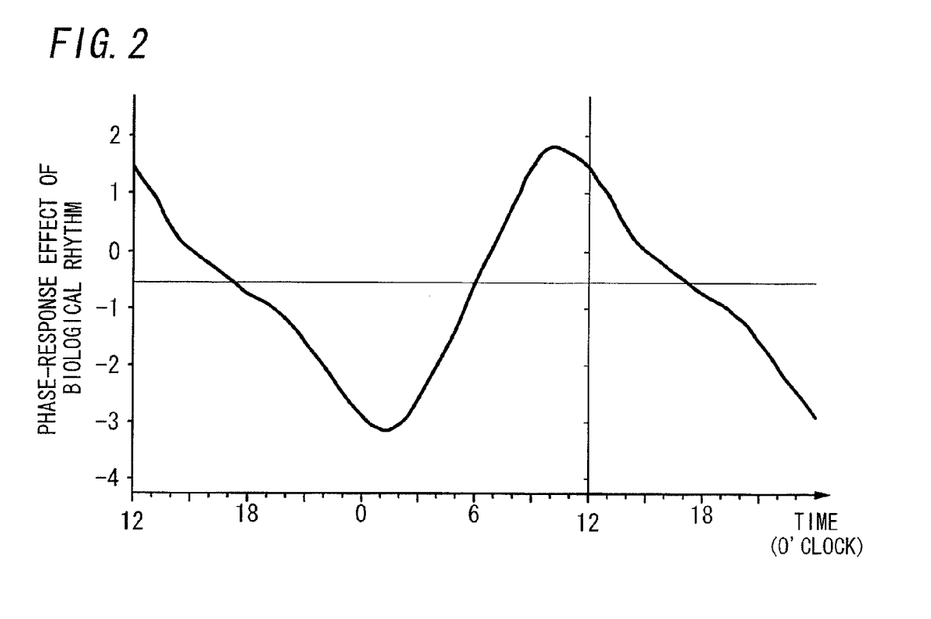
FIG. 2 is a graph chart depicting a relationship of phase-response effects versus time in the first embodiment.

People have biological clocks with biological rhythm such as circadian rhythm, and the biological rhythm has approximately a 24-hour period. It is known that the biological rhythm has a synchronizer of light such as sunlight, illumination light and the like, and synchronizes with light-dark cycle of the light. That is, the biological rhythm has phase-response effect influenced by the light, and the phase-response effect has different direction and amount of change by timing subjected to the light (see FIG. 2). If a person is subjected to light before noon, a phase of the person's biological rhythm is advanced, and therefore the biological rhythm shifts to what is called a morning pattern and is adjusted properly. By contraries, if a person is subjected to light at night, a phase of the person's biological rhythm is retarded, and therefore the biological rhythm shifts to what is called a night pattern and is disturbed. Thus, adjusting biological rhythm properly requires receiving light sufficiently before noon and decreasing amount of light to be received at night.

Biological rhythm adjusts the release of melatonin that is a hormone produced at the pineal body in the hypothalamus of a brain, and the melatonin is an important marker for the biological rhythm. It has been reported that melatonin has a stimulating effect on body temperature decrease and maintenance of sleep at night. The melatonin is barely released in daylight, and a blood concentration of melatonin increase from night to reach a peak from night to early morning.

Figure 3:
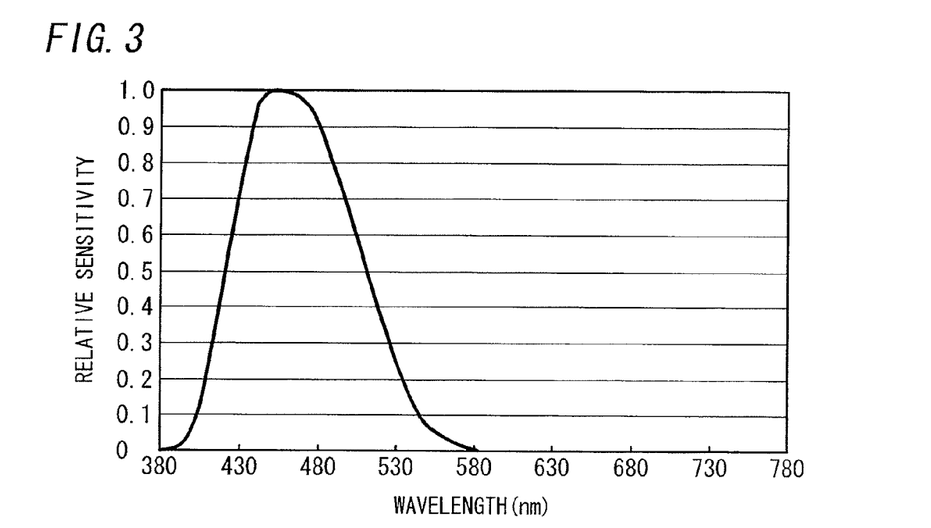
FIG. 3 is a graph chart depicting a relationship of inhibition of melatonin secretion versus wavelengths (action spectrum) in the first embodiment.

Melatonin is released at night, but it has been reported that light prevents melatonin from being released. FIG. 3 shows an action spectrum (an action curve) concerning inhibition of melatonin secretion. The action spectrum shows wavelengths of light in a horizontal axis and relative sensitivity with respect to inhibition of melatonin secretion in a vertical axis, where melatonin secretion is easily suppressed by a short wavelength optical range with a peak of 460 nm, namely by emitting a blue light.

In order to quantify action (effect) of the spectrum with respect to biological rhythm, Deutsche Industrie Normen (DIN) suggests the following expression (DIN V 5031-100):

$$\alpha = \frac{\int_{\lambda 1}^{\lambda 2} X(\lambda) \cdot B(\lambda) \, d\lambda}{\int_{380\,nm}^{780\,nm} X(\lambda) \cdot V(\lambda) \, d\lambda},$$

where $\alpha$ (hereinafter referred to as a "biological action level") is an effect extent per unit illumination which influences inhibition of melatonin secretion, $\lambda$ is wavelength of light emitted from a light source, $X(\lambda)$ is spectrum irradiation illumination of the light source, $V(\lambda)$ is spectral luminous efficiency, and $B(\lambda)$ is relative sensitivity with respect to inhibition of melatonin secretion.

Figure 4:
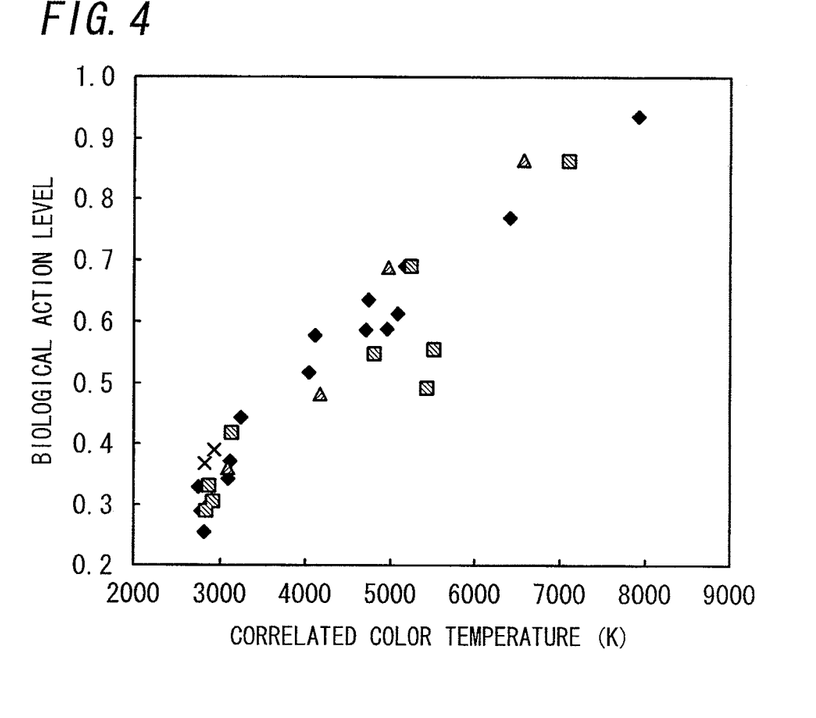
FIG. 4 is a graph chart depicting a relationship of biological action levels versus correlated color temperatures in the first embodiment.

FIG. 4 shows a relationship of emission of each of various light sources and biological action levels, where a diamond filled with black color (♦) represents a LED module formed of a printed circuit board and a plurality of LED devices mounted on the board, a square filled with hatches represents an LED light bulb, a triangle filled with hatches represents a fluorescent light lamp, and a x-mark (x) represents an incandescent lamp. As can be seen from FIG. 4, a correlation is between correlated color temperatures and biological action levels.

Figure 5:
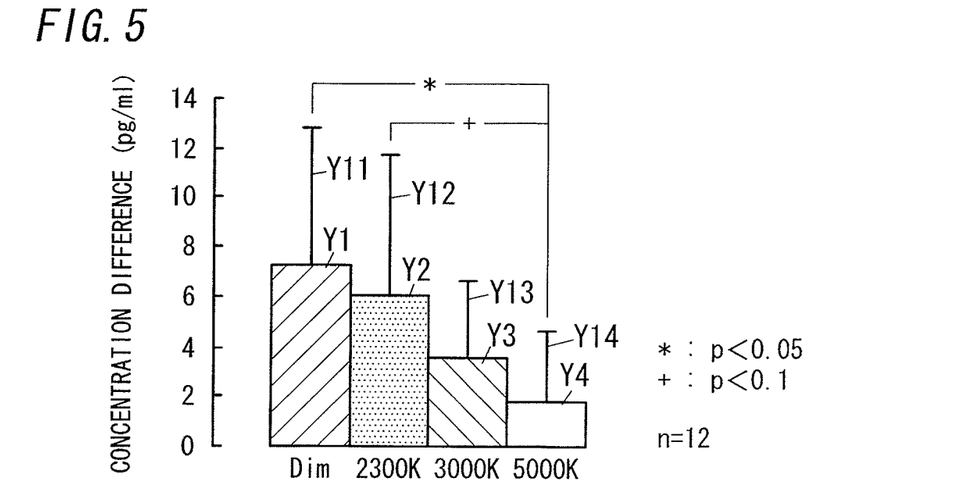
FIG. 5 is a graph chart depicting melatonin concentration differences before or after exposed to light in the first embodiment.

FIG. 5 is a bar chart showing saliva concentration differences of melatonin before or after exposed to light. In bars Y1 to Y4, correlated color temperatures of light emitted to subjects are different from each other. Bar Y1 shows a saliva concentration difference of melatonin before or after exposed to light in almost an extinction state (Dim). Bar Y2 shows a saliva concentration difference of melatonin before or after exposed to light of which correlated color temperature is 2300 K. Bar Y3 shows a saliva concentration difference of melatonin before or after exposed to light of which correlated color temperature is 3000 K. Bar Y4 shows a saliva concentration difference of melatonin before or after exposed to light of which correlated color temperature is 5000 K. Error bars Y11 to Y14 show standard deviations of results of bars Y1 to Y4, respectively. The concentration difference of melatonin in bar Y4 (5000 K) is significantly lower than that in bar Y1 (Dim). Marginally significant (p<0.08) is between bar Y4 (5000 K) and bar Y2 (2300 K). As can be seen from FIG. 5, inhibitory effect of melatonin secretion becomes lower as a correlated color temperature of light which influences the effect becomes lower.

Therefore, considering biological rhythm synchronizing with light-dark cycle of light and a relationship between correlated color temperatures and biological action levels, a light having a high correlated color temperature and a high illuminance is better adapted to biological rhythm in daylight, while a light having a low correlated color temperature and a low illuminance is better adapted to biological rhythm at night.

Figure 6:
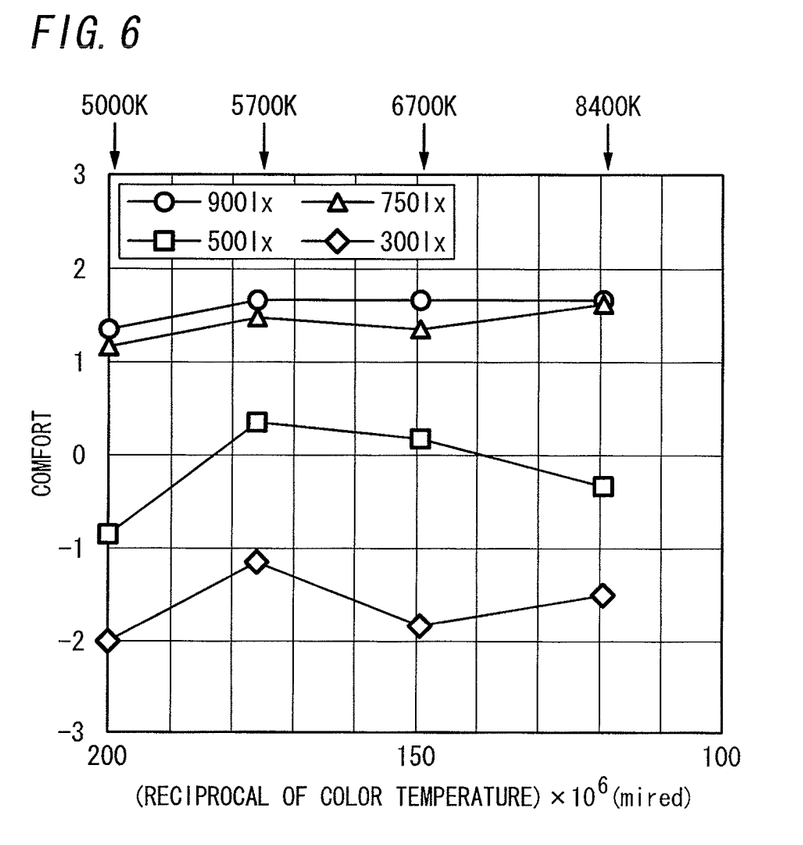
FIG. 6 is a graph chart depicting comfort evaluation results before noon in the first embodiment.
Figure 7:
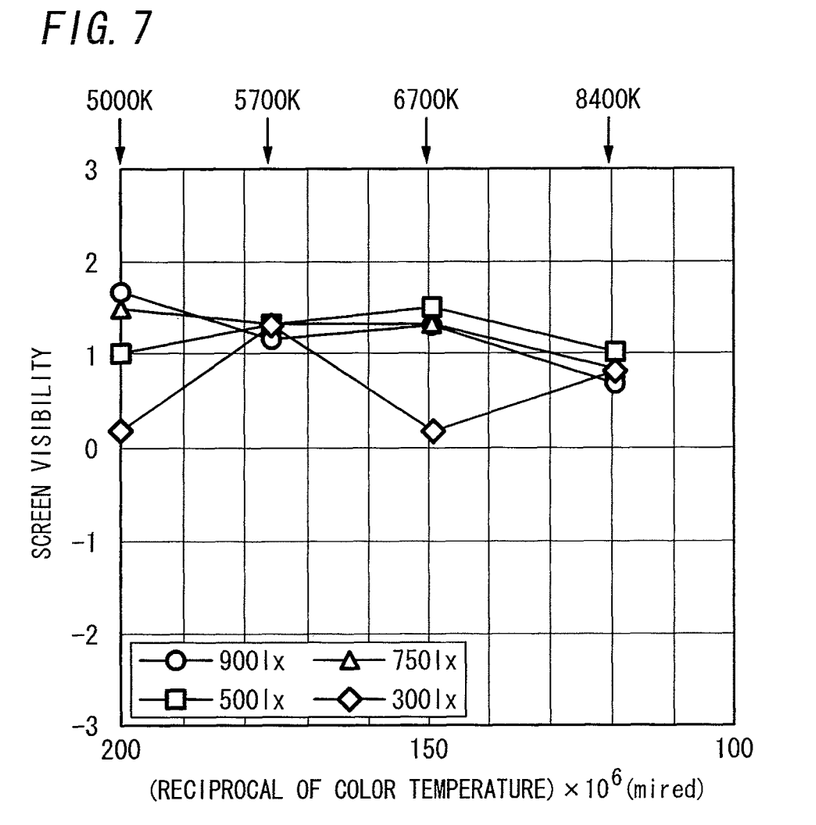
FIG. 7 is a graph chart depicting screen-visibility evaluation results before noon in the first embodiment.
Figure 8:
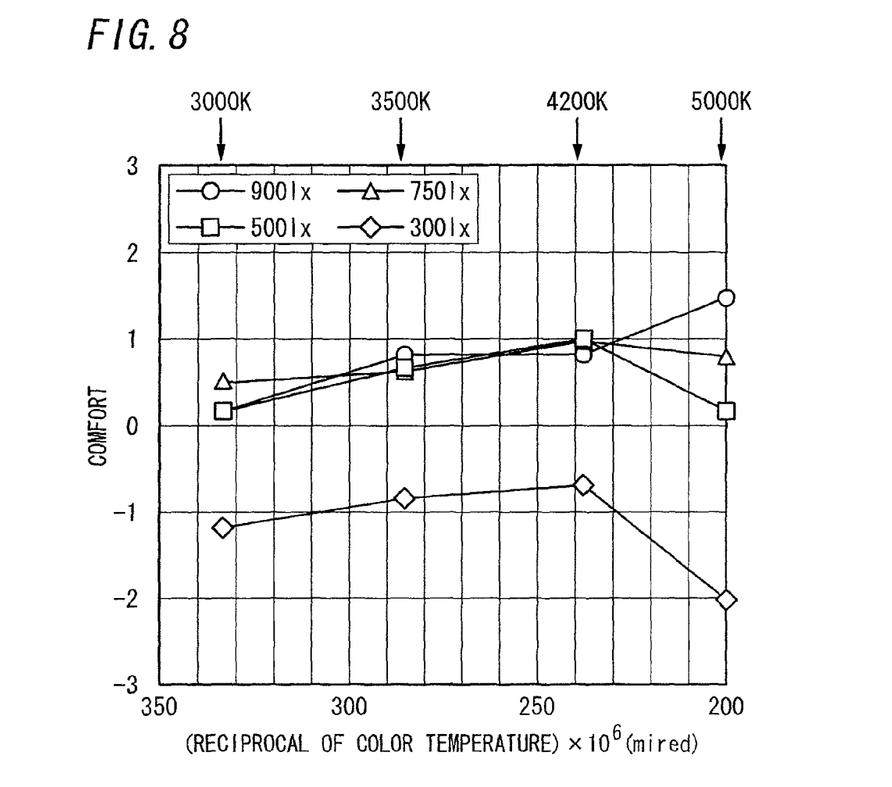
FIG. 8 is a graph chart depicting comfort evaluation results after noon in the first embodiment.

FIGS. 6 to 8 show experimental results of subjective evaluation on correlated color temperatures of a light source and illuminances in an installation space of the light source. The subjective evaluation was performed by 10 male subjects about comfort under various lighting conditions and screen visibility of a personal computer. In FIGS. 6 to 8, diamonds (◇) show results under an illuminance of 300 lx, squares (□) show results under an illuminance of 500 lx, triangles (△) show results under an illuminance of 750 lx, and circles (○) show results under an illuminance of 900 lx.

FIG. 6 shows comfort evaluation results of before noon. The comfort is evaluated by seven-grade of 3, 2, 1, 0, −1, −2, −3 in order of comfort superiority with respect to all combinations of correlated color temperatures of 5000 K, 5700 K, 6700 K and 8400 K and illuminances of 300 lx, 500 lx, 750 lx and 900 lx. According to comfort evaluation of FIG. 6, illuminance equal to or higher than about 500 lx is required in order to keep comfort before noon. Correlated color temperatures have little influence on comfort before noon as compared with illuminances.

FIG. 7 shows screen-visibility evaluation results with respect to a personal computer before noon. The screen-visibility is evaluated by seven-grade of 3, 2, 1, 0, −1, −2, −3 in order of screen-visibility with respect to all combinations of correlated color temperatures of 5000 K, 5700 K, 6700 K and 8400 K and illuminances of 300 lx, 500 lx, 750 lx and 900 lx. According to the screen-visibility evaluation results of FIG. 7, correlated color temperatures and illuminances have little influence on screen-visibility. In this regard, however, there were evaluation results that the correlated color temperature of 6700 K or more caused the screen to appear objectionable yellowish and made characters on the screen difficult to be seen. The evaluation that the screen appeared objectionable yellowish started from the correlated color temperature of 6700 K and became marked at the correlated color temperature of 8400 K.

FIG. 8 shows comfort evaluation results at night. The comfort is evaluated by seven-grade of 3, 2, 1, 0, −1, −2, −3 in order of comfort superiority with respect to all combinations of correlated color temperatures of 3000 K, 3500 K, 4200 K and 5000 K and illuminances of 300 lx, 500 lx, 750 lx and 900 lx. According to the comfort evaluation results of FIG. 8, illuminances of 300 lx or more is required in order to keep comfort at night. As a whole, high evaluations with respect to comfort at night were obtained in the correlated color temperature range from 3500 K to 4200 K. The illuminance difference in the illuminance of 500 lx or more has little effect on comfort. Therefore, the illuminance of approximately 300 lx or more is required in order to keep comfort at night. The illuminance of approximately 500 lx or less is also desirable for energy saving at night.

In the first embodiment, the lighting loads 2 are installed in an office (e.g., an office space or the like) where personal computers are put on workers' desks. The controller 1a of the lighting control device 1 is configured to perform the following lighting control in order to balance the light environment suitable for biological rhythm with energy-saving for working hours at such an office.

The operation display unit 3 is used to produce schedule information for controlling toning and dimming of the lighting loads 2 by user operation. The operation display unit 3 is configured to transmit the produced schedule information to each lighting control device 1. Each lighting control device 1 is configured to receive the schedule information from the operation display unit 3 to store the received schedule information in its own storage unit 1b. Each controller 1a is configured to control toning and dimming of corresponding lighting loads 2 in accordance with the schedule information stored in a corresponding storage unit 1b. A component for producing schedule information is not limited to the operation display unit 3. For example, schedule information may be produced through other terminal device.

Figure 9:
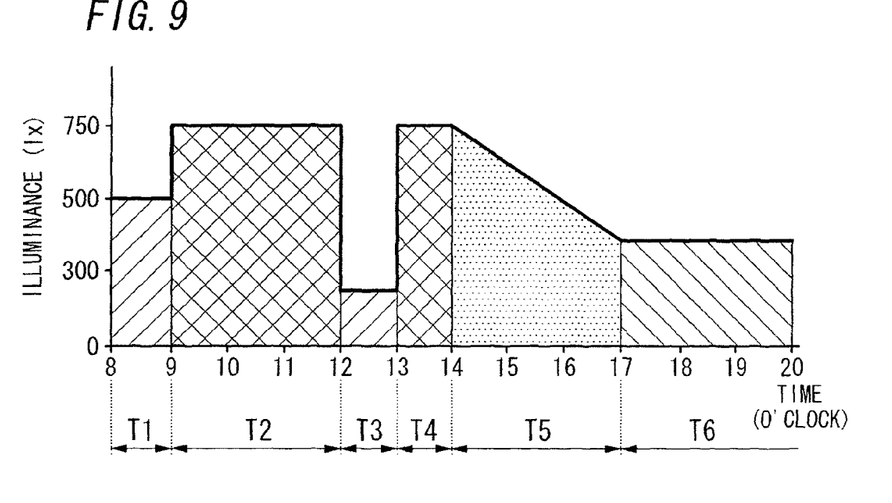
FIG. 9 is a graph chart depicting schedule information in the first embodiment.

The schedule information defines, for example, a schedule for toning and dimming as shown in FIG. 9. In a concrete example, the schedule information defines a time schedule (a timetable) showing times or time periods at each of which it will specify a correlated color temperature and a horizontal illuminance in the office by light to be emitted from each corresponding lighting load 2. Each horizontal illuminance in the office is an illuminance on a predetermined surface in the office (e.g., the top(s) of a desk(s) located around the center of the illumination range of a lighting system (A)). FIG. 9 shows only time schedule from 08:00 to 20:00 in the schedule information.

Each controller 1a includes a timer function for obtaining a current time and is configured to control toning and dimming of corresponding lighting loads 2 in accordance with the current time and the schedule information stored in a corresponding storage unit 1b.

Each lighting load 2 includes, as a light source, different kinds of LED devices 20 of which correlated color temperatures are different from each other. Each lighting control device 1 (storage unit 1b) previously has an output table that includes a plurality of parameter sets at arbitrary intervals over a period of time, and each of the parameter sets define values of electric currents that are supplied to LED devices 20 of each of corresponding lighting loads 2 and are equivalent to both a correlated color temperature and a horizontal illuminance at a corresponding interval (time period). For example, the parameter set at the interval from 09:00 to 12:00 in FIG. 9 defines values of electric currents that are supplied to LED devices 20 of each of corresponding lighting loads 2 and are equivalent to both the correlated color temperature of 6000 K and the horizontal illuminance of 750 lx at the interval. Each controller 1a is configured to adjust electric currents supplied to LED devices 20 of each of corresponding lighting loads 2 to values of a parameter set of a correlated color temperature and an illuminance in the output table. That is, each controller 1a performs timer control for performing predetermined toning and dimming control at a time previously determined by the schedule information. In short, the lighting control device 1 is configured to adjust a correlated color temperature and an illuminance obtained from a lighting load 2 by adjusting each light output of light source elements 20 of the lighting load 2.

At a time slot (office hours or working hours before noon) T2 from 09:00 (staring of office hours) to 12:00, each controller 1a adjusts a correlated color temperature and a horizontal illuminance in the office obtained from corresponding lighting loads 2, e.g., each of the corresponding lighting loads 2 to 6000 K and 750 lx, respectively. The time slot T2 corresponds to the first time slot of the present invention. Thus, by emitting light having a high correlated color temperature and a high illuminance to workers at the time slot T2, the workers can have activated biological rhythm and maintain wakefulness. In FIG. 9, each interval of cross-hatching represents a region corresponding to the correlated color temperature of 6000 K. That is, the cross-hatching intervals are the time slot from 09:00 to 12:00 and the time slot from 13:00 to 14:00.

It is desirable that the correlated color temperature of the lighting loads 2 at the time slot T2 be set to a higher value than neutral white of 4600 K to 5500 K specified in JIS 29112 (e.g., a higher value than 5500 K). In the schedule information, it is set to 6000 K. The correlated color temperature of fluorescent lamps mainly used in conventional offices is the neutral white, but the correlated color temperature of the lighting loads 2 is set to a higher correlated color temperature than the neutral white, thereby improving wakefulness as compared with the conventional neutral white.

It is also desirable that the correlated color temperature of the lighting loads 2 at the time slot T2 be set to a value equal to or less than daylight color of 5700 K to 7100 K specified in JIS Z9112 (e.g., a value equal to or less than 7100 K), in order to prevent a phenomenon that screens of personal computers used in the office appear yellowish.

It is desirable that the horizontal illuminance in the office at the time slot T2 be set to about 500 lx or more in order to keep comfort. In the schedule information, it is set to 750 lx.

In an example, the time slot T2 may be a time slot from the start time to around 12:00 from which a lunch break starts. That is, it is preferable that the first time slot is in a range from a time before noon (e.g., a starting time of work) to one o'clock after noon.

At a time slot (a time slot before office hours) T1 from 08:00 to 09:00 in the morning before office hours, each controller 1a adjusts a correlated color temperature and a horizontal illuminance in the office obtained from each corresponding lighting load 2 to 5000 K and 500 lx, respectively. The time slot T1 corresponds to the fourth time slot of the present invention. Thus, by reducing the illuminance in the office at the time slot T1 when a few workers are in the office as compared with the time slot T2, energy can be saved and workers' complaints can be suppressed. It is also possible to relax workers before working by decreasing the correlated color temperature at the time slot T1 as compared with the time slot T2. In FIG. 9, each interval of diagonally-right-up hatching represents a region corresponding to the correlated color temperature of 5000 K. That is, these intervals are the time slot from 08:00 to 09:00 and the time slot from 12:00 to 13:00.

At a time slot (lunch break time) T3 from 12:00 noon to 13:00, each controller 1a adjusts a correlated color temperature and a horizontal illuminance in the office obtained from each corresponding lighting load 2 to 5000 K and 200 lx, respectively. Thus, by reducing the illuminance in the office at the time slot T3 as compared with the time slot T2, energy can be saved. It is also possible to relax workers during lunch break by decreasing the correlated color temperature at the time slot T3 as compared with the time slot T2.

At a time slot (office hours or working hours afternoon) T4 from 13:00 (the restart time) to 14:00 in the afternoon, each controller 1a adjusts a correlated color temperature and a horizontal illuminance in the office obtained from each corresponding lighting load 2 to 6000 K and 750 lx, respectively. Thus, by emitting light having a high correlated color temperature and a high illuminance to workers like the time slot T2, the workers can have activated biological rhythm and maintain wakefulness. It is possible to prevent drowsiness around 13:00, what is called post-lunch dip. It is preferable that the time slot T4 be a time slot after noon including a time when the post-lunch dip tends to take place. Setting the time slot T4 to a time slot from the restart time to around 14:00 is effective.

At a time slot (office hours or working hours after noon) T5 from 14:00 (midafternoon) to 17:00 (early-evening), each controller 1a gradually decreases both of (i.e., cooperatively) a correlated color temperature and a horizontal illuminance in the office obtained from each corresponding lighting load 2. The time slot T5 corresponds to the second time slot of the present invention, after or just after the first time slot. In a concrete example, each controller 1a is configured to gradually decrease a correlated color temperature and a horizontal illuminance in the office, obtained from each corresponding lighting load 2, from 6000 K and 750 lx to 4000 K and 400 lx, respectively. That is, each controller 1a is configured to cooperatively and gradually decrease a correlated color temperature and a horizontal illuminance obtained from each corresponding lighting load 2 with the passage of time in the time slot T5. In FIG. 9, the interval of dots represents a region corresponding to the correlated color temperature decreased from 6000 K to 4000 K. That is, this interval is the time slot from 14:00 to 17:00.

It is desirable that a correlated color temperature of each lighting load 2 at the finish time of the time slot T5 is set to a lower value than the neutral white of 4600 K to 5500 K specified in JIS Z9112 (e.g., a lower value than 4600 K). It is set to 4000 K in the schedule information. The correlated color temperature of fluorescent lamps mainly used in conventional offices is the neutral white, but the correlated color temperature of the lighting loads 2 is set to a lower correlated color temperature than the neutral white, thereby giving consideration to biological rhythm as compared with the conventional neutral white.

It is also desirable that a correlated color temperature of each lighting load 2 at the finish time of the time slot T5 is set to a higher value than the light bulb color of 2600 K to 3250 K specified in JIS Z9112 (e.g., a higher value than 3250 K). It is set to 4000 K in the schedule information, thereby preventing work efficiency degradation at the office, namely addressing concern that workers needlessly relax when a correlated color temperature of each lighting load 2 is decreased beyond necessity.

It is desirable that a horizontal illuminance in the office at the finish time of the time slot T5 is set to approximately 300 lx or more and 500 lx or less in order to balance comfort with energy-saving at night. It is set to 400 lx in the schedule information.

Figure 10:
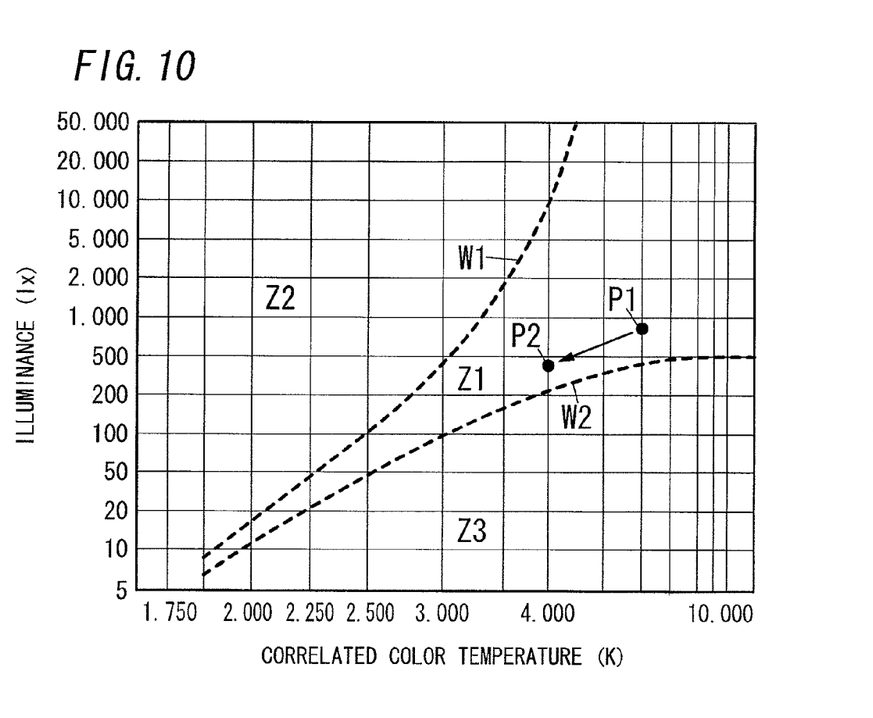
FIG. 10 is a graph chart depicting Kruithofs Curve in the first embodiment.

Gang control of a correlated color temperature and a horizontal illuminance at the time slot T5 is performed based on the Kruithofs Curve as shown in FIG. 10. In FIG. 10, the horizontal axis represents correlated color temperatures and the vertical axis represents illuminances. In the Kruithofs Curve, a region intervening between two curves W1 and W2 is a comfort region Z1 that gives people comfort. An outer side of the curve W1 at a side of high illuminance is a discomfort region Z2 that gives people sultry discomfort. An outer side of the curve W2 at a side of low illuminance is a discomfort region Z3 that gives people dismal discomfort. That is, each controller 1a is configured to gradually decrease a correlated color temperature and a horizontal illuminance obtained from each of corresponding lighting loads 2 so that the comfort region Z1 is maintained in the time slot T5. The gradual decrease suppresses discomfort and the negative influence on biological rhythm can be avoided. In the example of FIG. 10, each controller 1a changes a correlated color temperature and a horizontal illuminance obtained from each of corresponding lighting loads 2 from an operating point P1 [6000 K, 750 lx] to an operating point P2 [4000 K, 400 lx] in the time slot T5.

In short, the lighting control device (1) of the present invention is configured: to adjust a light output of at least one lighting load (2) to a first light output corresponding to a first correlated color temperature and a first illuminance in a first time slot (e.g., T2); and to decrease the light output of the lighting load (2) up to a second light output corresponding to a second correlated color temperature and a second illuminance with the passage of time (e.g., gradually, linearly or in a stepwise fashion) over a second time slot (e.g., T5) after the first time slot, the second light output, where the second correlated color temperature and the second illuminance are lower than the first correlated color temperature and the first illuminance, respectively. In an embodiment, the lighting control device (1) is configured to decrease the light output of the lighting load (2) up to the second light output from the first light output with the passage of time over the second time slot.

Thus, each controller 1a gradually shifts each light output of corresponding lighting loads 2 from a light output of a high correlated color temperature and a high illuminance to a light output of a low correlated color temperature and a low illuminance in consideration of biological rhythm in the time slot T5. In addition, each controller 1a performs control such that a correlated color temperature and a horizontal illuminance obtained from each of corresponding lighting loads 2 maintain the comfort region Z1 of the Kruithofs Curve in the time slot T5, thereby keeping space comfort. Each controller 1a also gradually decreases a horizontal illuminance obtained from each of corresponding lighting loads 2 in the time slot T5, thereby promoting energy savings as compared to the case that a high illuminance is kept over during every time slot of daytime.

At a time slot (office hours or working hours at night) T6 after the time slot T5, each controller 1a is configured to maintain the correlated color temperature and the horizontal illuminance at the finish time of the time slot T5 with respect to each of corresponding lighting loads 2. Specifically, each controller 1a adjusts the correlated color temperature and the horizontal illuminance to 4000 K and 400 lx, respectively in accordance with the schedule information. Therefore, lighting can be performed with consideration for biological rhythm by light having a low illuminance and a low correlated color temperature at the time slot T6. In FIG. 9, the interval of diagonally-right-down hatching represents a region corresponding to the correlated color temperature of 4000 K. It is desirable that the correlated color temperature at the time slot T6 is in a range from 3500 K to 4200 K receiving a high evaluation with respect to comfort at night. It is also miserable desirable that the horizontal illuminance at the time slot T6 is set to be approximately 300 lx or more and 500 lx or less in order to secure comfort at night and promoting energy saving.

Thus, each lighting control device 1 is configured to emit light having a high correlated color temperature and a high illuminance during daytime and to emit light having a low correlated color temperature and a low illuminance at night, with consideration for biological rhythm. In addition, each lighting control device 1 gradually decreases the horizontal illuminance at the time slot T5 without maintaining a high illuminance during every time slot of daytime, thereby promoting energy saving. That is, it is possible to balance the light environment suitable for the biological rhythm with energy-saving for working hours.

The installation location of a lighting system (A) equipped with a lighting control device 1 is not limited to an office. For example, the lighting system (A) may be installed in a workplace such as a workshop or the like.

Second Embodiment

Figure 11:
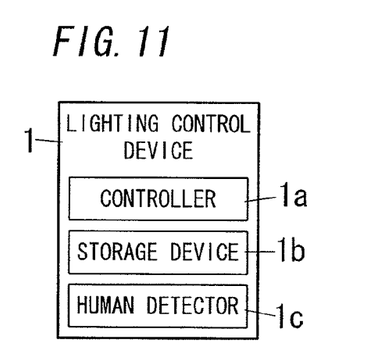
FIG. 11 is a block diagram of a lighting control device in accordance with a second embodiment of the present invention.

As shown in FIG. 11, a lighting control device 1 of the second embodiment is further provided with a human detector (e.g., a motion sensor) 1c in addition to the configuration of the first embodiment. For the purpose of clarity, like kind elements are assigned the same reference numerals as depicted in the first embodiment.

The human detector 1c is configured to detect the presence or nonpresence of a person(s) in an installation space of a lighting load(s) 2 (e.g., an office) to transmit a detection result to a controller 1a of the lighting control device 1. The controller 1a is configured to perform the following control based on the detection result of the human detector 1c.

When a person(s) is(are) present in the office, the controller 1a performs timer control in accordance with a schedule information like the first embodiment, thereby adjusting a correlated color temperature and a horizontal illuminance in the office obtained from at least one corresponding lighting load 2.

When no person is present in the office, the controller 1a adjusts a correlated color temperature and a horizontal illuminance in the office obtained from the lighting load(s) 2, as follows.

The controller 1a adjusts a correlated color temperature of the lighting load(s) 2 by the timer control based on the schedule information when no person is present in the office. That is, the correlated color temperature of the lighting load(s) 2 is adjusted by the timer control based on the schedule information irrespective of the presence or nonpresence of a person(s) in the office.

When no person is present in the office, the controller 1a also more decreases the horizontal illuminance in the office than a horizontal illuminance at a current time under the timer schedule. For example, when no person is present in the office at a time slot (office hours or working hours before noon) T2, the controller 1a decreased or changes the horizontal illuminance (of 750 lx) in the office to a lower value than 750 lx. Similarly, when no person is present in the office at a time slot (office hours or working hours after noon) T5, the controller 1a more decreases the horizontal illuminance in the office than a horizontal illuminance at a current time set in the schedule information. If a person(s) is(are) detected in the office, the controller 1a increases the horizontal illuminance in the office to a horizontal illuminance at a current time in accordance with the schedule information.

In short, the lighting control device 1 is configured to adjust a light output of the lighting load(s) 2 to the first light output in the first time slot and also to decrease the light output of the lighting load(s) 2 up to the second light output with the passage of time in the second time slot, when the human detector 1c is detecting the presence of a person(s). The lighting control device 1 is also configured to change the first light output to a light output corresponding to the first correlated color temperature and a lower illuminance than the first illuminance in the first time slot and also to change the second light output to a light output corresponding to the second correlated color temperature and a lower illuminance than the second illuminance in the second time slot, when the human detector 1c is detecting the nonpresence of a person.

In the second embodiment, when no person is present in the office, the controller 1a decreases the horizontal illuminance in the office, thereby promoting energy saving. In addition, if the controller 1a maintains the timer control based on the schedule information with respect to the correlated color temperature of the lighting load(s) 2, when a person(s) appears in the office, it is possible to suppress discomfort or uncomfortable feeling.

When a plurality of lighting systems (A) is installed in the same floor, the situation may occur that a person(s) is(are) present in an illumination range of a lighting system (A) but no person is present in illumination range(s) of other lighting system(s) (A). In this case, correlated color temperatures of the lighting systems (A) are the same as each other, and it is therefore possible to suppress discomfort caused by difference between color of light emitted to a person(s) in the floor from the aforementioned lighting system (A) and color of light from the other lighting system(s).

Third Embodiment

Figure 12:
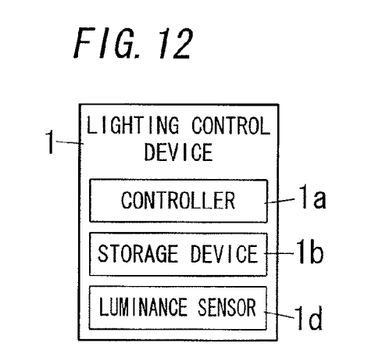
FIG. 12 is a block diagram of a lighting control device in accordance with a third embodiment of the present invention.

As shown in FIG. 12, a lighting control device 1 of the third embodiment is further provided with a luminance sensor (a brightness sensor) 1d in addition to the configuration of the first embodiment. For the purpose of clarity, like kind elements are assigned the same reference numerals as depicted in the first embodiment.

A lighting load(s) 2 of a lighting system(s) (A) in the third embodiment is(are) installed in an office with a window(s). Therefore, the illuminance in the office changes in response to an incoming light such as sunlight or the like from outside.

The luminance sensor 1d is configured to detect (measure) a horizontal illuminance on a predetermined surface in the office (e.g., the top(s) of a desk(s) located around the center of the illumination range of a lighting system(s) (A)) to transmit a detection result to a controller 1a of the lighting control device 1.

The controller 1a is configured to adjust the light output of the lighting load(s) 2 so that the detection result becomes a horizontal illuminance set in the schedule information. It is therefore possible to decrease the light output of the lighting load(s) 2 when the light enters the office from outside, thereby adjusting the horizontal illuminance in the office to a horizontal illuminance based on the schedule information.

The controller 1a is also configured to adjust the correlated color temperature of the lighting load(s) 2 by the timer control based on the schedule information when controlling the light output of the lighting load(s) 2 based on the detection result of the luminance sensor 1d. That is, the controller 1a maintains the timer control based on the schedule information with respect to the correlated color temperature of the lighting load(s) 2 even when changing the light output of the lighting load(s) 2 based on the detection result of the luminance sensor 1d. For example, when a plurality of lighting systems (A) is installed in the same floor, the situation may occur that light enters the illumination range of a lighting system (A) at the window(s) from outside but light does not enter the illumination range of other lighting system(s) (A) at a wall. In this case, correlated color temperatures of the lighting systems (A) are the same as each other, and it is therefore possible to suppress discomfort caused by difference between color of light from the lighting system (A) at the window(s) and color of light from the lighting system(s) (A) at the wall.

The invention claimed is:

1. A lighting system, comprising:
a lighting load including a plurality of light source elements having different kinds of correlated color temperatures; and
a lighting control device configured
to adjust a light output of the lighting load to a first light output corresponding to a first correlated color temperature and a first illuminance in a first time slot, and
to decrease the light output of the lighting load up to a second light output with the passage of time in a second time slot after the first time slot, the second light output corresponding to a second correlated color temperature and a second illuminance,
wherein the lighting control device is configured to cooperatively decrease, in the second time slot, a correlated color temperature and an illuminance obtained from the lighting load, the cooperative decrease is performed within a target region defined by Kruithof's Curve in which a horizontal axis represents the correlated color temperature and a vertical axis represents an illuminance, wherein the target re ion is bounded b a first curve that delimits an upper side of the target region and a second curve that delimits a lower side of the target region.

2. The lighting system of claim 1,
wherein the lighting control device is configured to adjust a correlated color temperature and an illuminance obtained from the lighting load by adjusting each light output of the light source elements.

3. The lighting system of claim 1, wherein the first correlated color temperature is higher than a color temperature of neutral white color.

4. The lighting system of claim 1, wherein the first correlated color temperature is equal to or lower than a color temperature of daylight color.

5. The lighting system of claim 1, wherein the first illuminance is a horizontal illuminance of 500 lx or more in an installation space of the lighting load.

6. The lighting system of claim 1, wherein the start of the second time slot is a time between one and three o'clock after noon.

7. The lighting system of claim 1, wherein the second correlated color temperature is lower than a color temperature of neutral white color.

8. The lighting system of claim 1, wherein the second correlated color temperature is higher than a color temperature of light bulb color.

9. The lighting system of claim 1, wherein the second illuminance is a horizontal illuminance of 300 lx or more and 500 lx or less in the installation space of the lighting load.

10. The lighting system of claim 1, wherein the lighting control device is further configured to decrease the light output of the lighting load to a third illuminance lower than the first illuminance in a third time slot between the first and second time slots.

11. The lighting system of claim 1, further comprising a human detector configured to detect the presence or nonpresence of a person in an installation space of the lighting load,
wherein the lighting control device is configured:
to adjust a light output of the lighting load to the first light output in the first time slot and also to decrease the light output of the lighting load up to the second light output with the passage of time in the second time slot, when the human detector is detecting the presence of a person; and
to change the first light output to a light output corresponding to the first correlated color temperature and a lower illuminance than the first illuminance in the first time slot and also to change the second light output to a light output corresponding to the second correlated color temperature and a lower illuminance than the second illuminance in the second time slot, when the human detector is detecting the nonpresence of a person.

12. The lighting system of claim 1, further comprising a luminance sensor configured to sense illuminance in an installation space, capable of receiving light from an outside, of the lighting load,
wherein the lighting control device is configured to control the light output of the lighting load based on the illuminance sensed with the luminance sensor.

13. The lighting system of claim 1, wherein the lighting control device is configured to adjust the light output of the lighting load to a fourth illuminance lower than the first illuminance in a fourth time slot just before the first time slot.

14. The lighting system of claim 1,
wherein the first curve passes approximately through points having coordinates of: 2000 K and 17 lx, 3000 K and 500 lx, and 4400 K and 50,000 lx, on the horizontal axis and the vertical axis, respectively, and
the second curve passes approximately through points having coordinates of: 2000 K and 6 lx, 3000 K and 100 lx, and 8000 K and 500 lx, on the horizontal axis and the vertical axis, respectively.

15. The lighting system of claim 1, wherein the first curve and second curve diverge with increasing temperature.

16. A lighting control device, configured to adjust a light output of a lighting load to a first light output corresponding to a first correlated color temperature and a first illuminance in a first time slot, and
To decrease the light output of the light load up to a second light output with the passage of time in a second time slot after the first time slot, the second light output corresponding to a second correlated color temperature and a second illuminance,
wherein the lighting control device is configured to cooperatively decrease, in the second time slot, a correlated color temperature and an illuminance obtained from the lighting load, the cooperative decrease is performed within a target region defined by Kruithof's Curve in which a horizontal axis represents the correlated color temperature and a vertical axis represents an illuminance, wherein the target region is bounded by a first curve that delimits an upper side of the target region and a second curve that delimits a lower side of the target region.

17. The lighting control device of claim 16,
wherein the first curve passes approximately through points having coordinates of: 2000 K and 17 lx, 3000 K and 500 lx, and 4400 K and 50,000 lx, on the horizontal axis and the vertical axis, respectively, and
the second curve passes approximately through points having coordinates of: 2000 K and 6 lx, 3000 K and 100 lx, and 8000 K and 500 lx, on the horizontal axis and the vertical axis, respectively.

18. The lighting control device of claim 16, wherein the first curve and second curve diverge with increasing temperature.

* * * * *